(12) United States Patent
Mitsuno et al.

(10) Patent No.: US 9,566,761 B2
(45) Date of Patent: *Feb. 14, 2017

(54) LAYERED NONWOVEN FABRIC, AND METHOD FOR PRODUCING LAYERED NONWOVEN FABRIC

(71) Applicant: Unicharm Corporation, Ehime (JP)

(72) Inventors: Satoshi Mitsuno, Kagawa (JP); Jun Okuda, Kagawa (JP); Noritomo Kameda, Kagawa (JP)

(73) Assignee: Unicharm Corporation, Ehime (JP)

( * ) Notice: Subject to any disclaimer, the term of this patent is extended or adjusted under 35 U.S.C. 154(b) by 101 days.

This patent is subject to a terminal disclaimer.

(21) Appl. No.: 14/346,929

(22) PCT Filed: Sep. 26, 2012

(86) PCT No.: PCT/JP2012/075588
§ 371 (c)(1),
(2) Date: Mar. 24, 2014

(87) PCT Pub. No.: WO2013/047890
PCT Pub. Date: Apr. 4, 2013

(65) Prior Publication Data
US 2014/0234575 A1   Aug. 21, 2014

(30) Foreign Application Priority Data

Sep. 30, 2011   (JP) .................. 2011-216877

(51) Int. Cl.
*B32B 3/30* (2006.01)
*B32B 5/26* (2006.01)
(Continued)

(52) U.S. Cl.
CPC .............. *B32B 3/30* (2013.01); *A61F 13/513* (2013.01); *A61F 13/5116* (2013.01);
(Continued)

(58) Field of Classification Search
CPC ....................................................... B32B 3/30
See application file for complete search history.

(56) References Cited

U.S. PATENT DOCUMENTS

2004/0140047 A1   7/2004   Sato et al.
2004/0214498 A1*  10/2004  Webb ................ D01F 8/06
                                                442/329

(Continued)

FOREIGN PATENT DOCUMENTS

EP   1 419 754 A1   5/2004
EP   2034071 A1     3/2009

(Continued)

OTHER PUBLICATIONS

International Search Report from corresponding PCT application No. PCT/JP2012/075588 dated Dec. 18, 2012 (1 pg).

*Primary Examiner* — William P Watkins, III
(74) *Attorney, Agent, or Firm* — Brinks Gilson & Lione

(57) ABSTRACT

A layered nonwoven fabric with excellent feel on the skin and liquid permeability, and a method for producing the layered nonwoven fabric. The layered nonwoven fabric includes an upper layer consisting of a first nonwoven fabric and a lower layer consisting of a second nonwoven fabric. The layered nonwoven fabric has a first surface on the first nonwoven fabric side with a plurality of protrusions and recesses and a second surface on the second nonwoven fabric side. The protrusions on the first surface have a higher basis weight than the recesses on the first surface, and the protrusions on the first surface have a lower fiber density than the recesses on the first surface.

8 Claims, 7 Drawing Sheets

(51) Int. Cl.
*D04H 3/16* (2006.01)
*B29C 55/18* (2006.01)
*B32B 5/04* (2006.01)
*B32B 5/14* (2006.01)
*B32B 3/26* (2006.01)
*A61F 13/511* (2006.01)
*A61F 13/513* (2006.01)
*B32B 5/02* (2006.01)
*D06B 1/02* (2006.01)
*D06C 3/06* (2006.01)
*D06C 15/00* (2006.01)
*B32B 38/00* (2006.01)

(52) U.S. Cl.
CPC .. *A61F 13/51104* (2013.01); *A61F 13/51108* (2013.01); *B29C 55/18* (2013.01); *B32B 3/26* (2013.01); *B32B 3/263* (2013.01); *B32B 3/266* (2013.01); *B32B 5/022* (2013.01); *B32B 5/04* (2013.01); *B32B 5/145* (2013.01); *B32B 5/26* (2013.01); *D04H 3/16* (2013.01); *D06B 1/02* (2013.01); *D06C 3/06* (2013.01); *D06C 15/00* (2013.01); *A61F 2013/51178* (2013.01); *A61F 2013/51333* (2013.01); *A61F 2013/51372* (2013.01); *B32B 2038/0028* (2013.01); *B32B 2262/02* (2013.01); *B32B 2305/20* (2013.01); *B32B 2555/02* (2013.01); *Y10T 428/24322* (2015.01); *Y10T 428/24562* (2015.01); *Y10T 428/24603* (2015.01); *Y10T 428/24612* (2015.01)

(56) References Cited

U.S. PATENT DOCUMENTS

2008/0085399 A1* 4/2008 Noda ................. B32B 3/30
                                        428/167
2009/0092797 A1   4/2009 Sato et al.

FOREIGN PATENT DOCUMENTS

| EP | 2034072 A1 | 3/2009 |
|---|---|---|
| JP | 08-109564 | 4/1996 |
| JP | 2004-174234 | 6/2004 |
| WO | WO 2012/121123 A1 | 9/2012 |

\* cited by examiner

LAYERED NONWOVEN FABRIC, AND METHOD FOR PRODUCING LAYERED NONWOVEN FABRIC

RELATED APPLICATION

This application is a 35 U.S.C. §371 national phase filing of International Patent Application No. PCT/JP2012/075588, filed Sep. 26, 2012, through which and to which priority is claimed under 35 U.S.C. §119 to Japanese Patent Application No. 2011-216877, filed Sep. 30, 2011.

TECHNICAL FIELD

The present disclosure relates to a layered nonwoven fabric and to a method for producing the layered nonwoven fabric.

BACKGROUND ART

Nonwoven fabrics are used in absorbent articles, such as sanitary products and disposable diapers, cleaning products, such as wipes and wipers, and medical goods, such as masks, and such products employ nonwoven fabrics with a performance suitable for the purpose of the products and their intended location of use.

With absorbent articles, for example, it is necessary to employ nonwoven fabrics that are capable of expanding and contracting in response to bodily movement during wear or use, without creating an uncomfortable feeling for the user. Disposable diapers require nonwoven fabrics with high elasticity and strength sufficient to prevent tearing during extension, as well as excellent feel on the skin and liquid permeability.

Nonwoven fabrics exhibiting the desired performance in such absorbent articles are usually designed for each individual product and produced from a net or the like. From the viewpoint of production cost and environmental protection, therefore, it is preferred for a nonwoven fabric having the desired performance to be one that can be easily produced by modification of a commercially available nonwoven fabric, for example.

As an example of a nonwoven fabric with excellent resistance to liquid leakage, that can be produced from a commercially available nonwoven fabric, PTL 1 describes a method for producing a surface sheet for an absorbent article, wherein an upper layer is incorporated into the mesh section between a first roll with an irregular peripheral surface and a second roll with an irregular peripheral surface which has a shape that meshes with the irregular shape of the first roll, to form the upper layer into an irregular shape, and the upper layer is held by aspiration on the peripheral surface of the first roll while in the irregularly formed state while being laminated with a lower layer, the lower layer being bonded to the upper layer on the protrusions of the first roll. It also describes a surface sheet produced by the method.

CITATION LIST

Patent Literature

PTL 1 Japanese Unexamined Patent Publication No. 2004-174234

SUMMARY OF INVENTION

Technical Problem

With the surface sheet described in PTL 1, however, although absorbed excreta and the like do not easily migrate in the in-plane direction of the surface sheet due to the irregular shape, i.e. lateral leakage is low, the fiber density in the recesses is high and liquid permeability in the thickness direction tends to be poor.

Furthermore, with the surface sheet described in PTL 1, the joining sections are formed by shaping and therefore tend to be hard with an inferior feel on the skin.

It is therefore an object of the present disclosure to provide a layered nonwoven fabric with excellent feel on the skin and liquid permeability, and a method for producing the layered nonwoven fabric.

Solution to Problem

As a result of diligent research directed towards solving the problems described above, the present inventors have found a layered nonwoven fabric comprising an upper layer consisting of a first nonwoven fabric and a lower layer consisting of a second nonwoven fabric, wherein the first nonwoven fabric and second nonwoven fabric are each composed of extendable fibers, and some of the extendable fibers of the first nonwoven fabric are tangled with some of the extendable fibers of the second nonwoven fabric, the layered nonwoven fabric having a first surface on the first nonwoven fabric side with a plurality of protrusions and recesses and a second surface on the second nonwoven fabric side, the protrusions on the first surface having a higher basis weight than the recesses on the first surface, and the protrusions on the first surface having a lower fiber density than the recesses on the first surface.

Advantageous Effects of Invention

The layered nonwoven fabric of the present disclosure has excellent feel on the skin and liquid permeability.

DESCRIPTION OF EMBODIMENTS

The layered nonwoven fabric of the present disclosure, and the method for producing the layered nonwoven fabric, will now be explained in detail.

[Layered Nonwoven Fabric]

Figure 1:
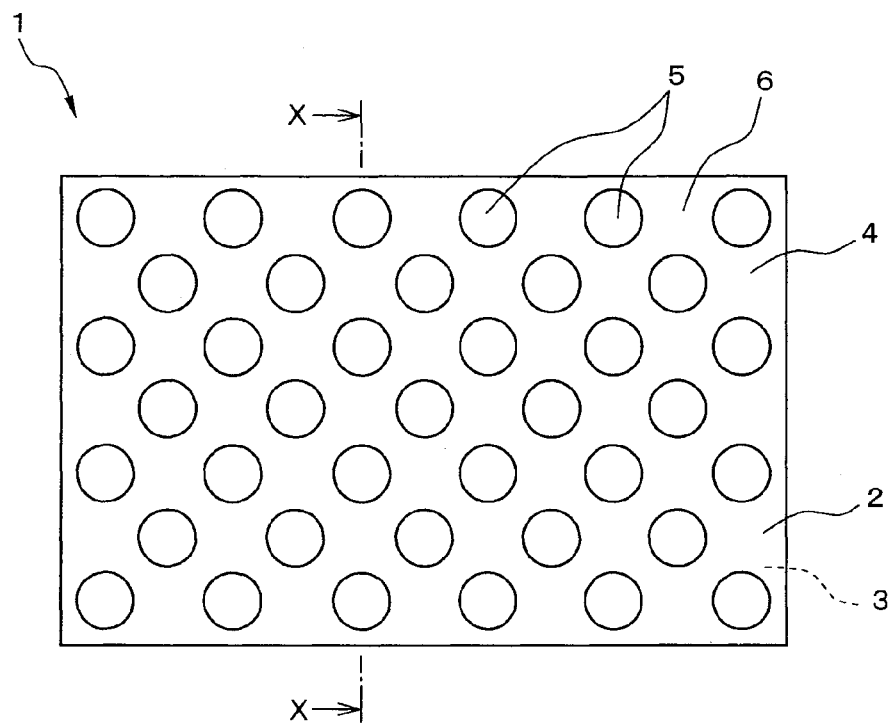
FIG. 1 is a diagram of an embodiment of the layered nonwoven fabric of the present disclosure, as viewed from the first surface.

FIG. 1 is a diagram of an embodiment of the layered nonwoven fabric of the present disclosure, as viewed from the first surface.

The layered nonwoven fabric 1 shown in FIG. 1 comprises an upper layer 2 consisting of a first nonwoven fabric, and a lower layer 3 consisting of a second nonwoven fabric. In the layered nonwoven fabric 1 shown in FIG. 1, the first nonwoven fabric and second nonwoven fabric are each composed of extendable fibers. The layered nonwoven fabric 1 comprises a first surface 4 with a plurality of protrusions 5 and recesses 6 on the first nonwoven fabric side.

Figure 2:
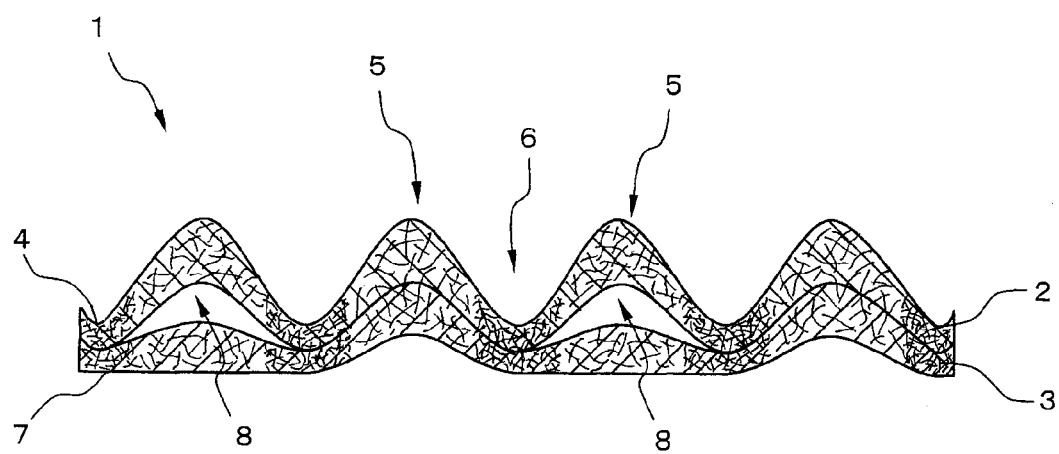
FIG. 2 is a cross-sectional view of the layered nonwoven fabric 1 shown in FIG. 1 along X-X.

FIG. 2 is a cross-sectional view of the layered nonwoven fabric 1 shown in FIG. 1 along X-X. In FIG. 2, the layered nonwoven fabric 1 comprises a first surface 4 with a plurality of protrusions 5 and recesses 6 on the first nonwoven fabric side, and a second surface 7 on the second nonwoven fabric side. The protrusions 5 on the first surface 4 have a higher basis weight than the recesses 6 on the first surface 4. Also in FIG. 2, some of the extendable fibers of the first nonwoven fabric are tangled with some of the extendable fibers of the second nonwoven fabric.

Having some of the extendable fibers of the first nonwoven fabric tangled with some of the extendable fibers of the second nonwoven fabric to anchor the upper layer and lower layer provides an advantage, in that liquid permeability is not inhibited compared to anchoring the upper layer and lower layer using an adhesive, such as a hot-melt.

In the layered nonwoven fabric, the protrusions on the first surface have a higher basis weight than the recesses on the first surface and the protrusions on the first surface also have a lower fiber density than the recesses on the first surface, thereby allowing the layered nonwoven fabric to exhibit superior feel on the skin and liquid permeability.

The reason for this is as follows.

Since the protrusions on the first surface have a higher basis weight than the recesses on the first surface in the layered nonwoven fabric, the recesses on the first surface have a lower amount of fibers in the thickness direction of the layered nonwoven fabric compared to the protrusions on the first surface, and therefore the layered nonwoven fabric has excellent liquid permeability in its thickness direction.

In addition, since the protrusions on the first surface have a lower fiber density than the recesses on the first surface of the layered nonwoven fabric, the protrusions that more frequently contact the skin exhibit greater softness, and therefore the layered nonwoven fabric has excellent feel on the skin.

The basis weight of the protrusions and recesses on the first surface can be calculated by cutting out a prescribed region of the protrusions and recesses and dividing their mass (g) by their area ($m^2$). A sharp blade, for example, spare blade "H-100" for KOKUYO cutter knife "HA-B" can be used to cut out the protrusions and recesses.

As used herein, the protrusion and recess can be divided by the line which is extending in the thickness direction of the layered nonwoven, and is passing the point having the intermediate thickness between the thickness of the protrusion and the thickness of recess in the layered nonwoven.

The fiber density of the protrusions and recesses on the first surface can be visually judged based on a photograph of the cross-section of the layered nonwoven fabric taken with an electron microscope or the like.

The cross-section of the layered nonwoven fabric can be obtained by dipping the layered nonwoven fabric into liquid nitrogen for 30 seconds, and cutting out it by a sharp blade, for example, spare blade "H-100". In addition, the cross-section can be imaged at 15× to 30× magnification using an electron microscope, for example, a Real Surface View VE7800 electron microscope by Keyence.

As used herein, the term "tangled" used in regard to the extendable fibers means that some of the extendable fibers of the first nonwoven fabric are in a wrapped state with some of the extendable fibers of the second nonwoven fabric; ie the respective fibers are twisted together into a confused mass. The preferred degree of tangling will differ depending on the purpose of use of the layered nonwoven fabric of the present disclosure, but when the layered nonwoven fabric is to be used in the top sheet of an absorbent article, for example, the first nonwoven fabric and the second nonwoven fabric may have a degree of intertangling represented by a peel strength of preferably between about 0.05 N/25 mm and about 15 N/25 mm and more preferably a peel strength of between about 0.1 N/25 mm and about 15 N/25 mm.

By having a degree of intertangling represented by this range of peel strength, the layered nonwoven fabric will be easily deformed during use and will exhibit excellent feel on the skin.

Here, "N/25 mm" means the tensile strength (N) per 25 mm width.

The peel strength can be measured in the following manner.

(1) A tensile tester is prepared with the chuck distance set to 40 mm and the chuck pull rate set to 500 mm/min.

(2) A sample is cut to 150 mm×25 mm (machine direction×cross-machine direction which is perpendicular to the machine direction).

(3) The upper layer and lower layer are peeled to about 30 mm from one end of the transport edge of the sample.

(4) The peeled upper layer is set in the upper chuck of the tensile tester, and set so as to be sandwiched in the chuck to a depth of about 10 mm.

(5) Similarly, the peeled lower layer is set in the lower chuck of the tensile tester, and set so as to be sandwiched in the chuck to a depth of about 10 mm.

(6) The tensile test is started with a chuck pull rate of 500 mm/min, and the tensile test is conducted until the chuck distance reaches 190 mm.

(7) The maximum tensile strength within a displacement of 150 mm is recorded.

(8) This procedure is further repeated 4 times, and the mean value for the total of 5 maximum tensile strengths is calculated.

The tensile tester used may be, for example, a Model AG-1KNI autograph tensile tester by Shimadzu Corp.

The preferred ranges for the number densities of the recesses and protrusions on the first surface will differ depending on the purpose of use of the layered nonwoven fabric of the present disclosure. For example, considered from the viewpoint of the layered nonwoven fabric production process, when the support described hereunder is a support with a plurality of roughly circular openings arranged in a zigzag shape, such as a punching plate, the layered nonwoven fabric may have on the first surface one recess corresponding to the non-opening sections of the punching plate, and a plurality of roughly circular protrusions corresponding to the openings of the punching plate.

Considering the structure of the punching plate, the protrusions on the first surface may be present at a number density of about 1 to about 500/cm$^2$.

Also, when the support described hereunder is a support having a predetermined shape and arrangement of projections and depressions, the layered nonwoven fabric may have a plurality of ridge-shaped protrusions and a plurality of furrow-shaped recesses on the first surface, with the number density of the ridge-shaped protrusions and the number density of the furrow-shaped recesses largely determined by the pitch of the fluid nozzle, and the ridge-shaped protrusions and furrow-shaped recesses may be present at a number density of about 1 to about 10/cm$^2$.

According to one embodiment of the layered nonwoven fabric of the present disclosure, as shown in FIG. 1, a plurality of circular protrusions 5 are arranged in a zigzag fashion in a unitary (single) recess 6 on the first surface.

Examples of such zigzag patterns include 60° zigzags, square zigzags and parallel forms.

According to another embodiment of the layered nonwoven fabric of the present disclosure, the protrusions on the first surface may be ridges and the recesses on the first surface may be furrows, with the ridges and furrows arranged in an alternating manner.

According to the embodiment shown in FIG. 2, at least some of the protrusions on the first surface 4 have spaces 8 formed between the upper layer 2 and lower layer 3.

The preferred range for the proportion of spaces in the protrusions will differ depending on the purpose of use of the layered nonwoven fabric of the present disclosure. For example, in an embodiment in which the layered nonwoven fabric is to be used as the top sheet of an absorbent article, preferably about 5-95%, more preferably about 10-90% and even more preferably about 15-85% of the protrusions have the spaces. If at least about 5% of the protrusions have spaces, the compression resistance is likely to be improved and the protrusions will be more resistant to collapse during use, while if no greater than about 95% of the protrusions have spaces, it is likely that the layered nonwoven fabric will not be too hard and the feel on the skin will be excellent.

Figure 3:
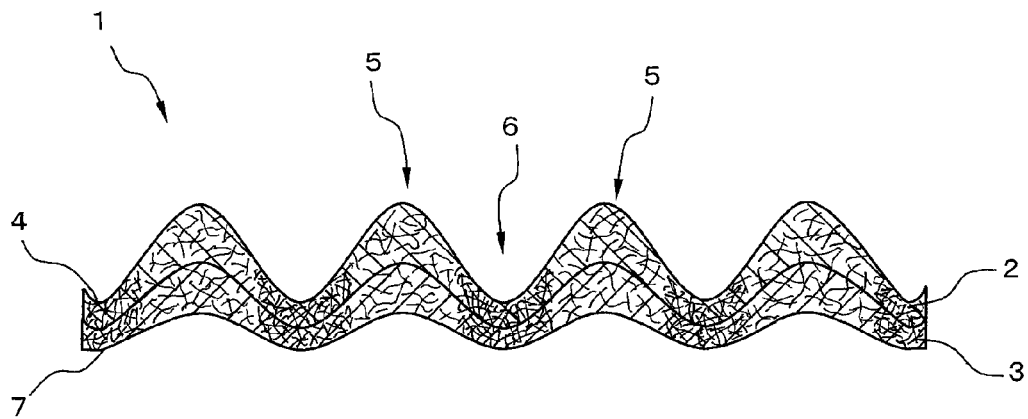
FIG. 3 is a cross-sectional view of another embodiment of the layered nonwoven fabric of the present disclosure.
Figure 4:
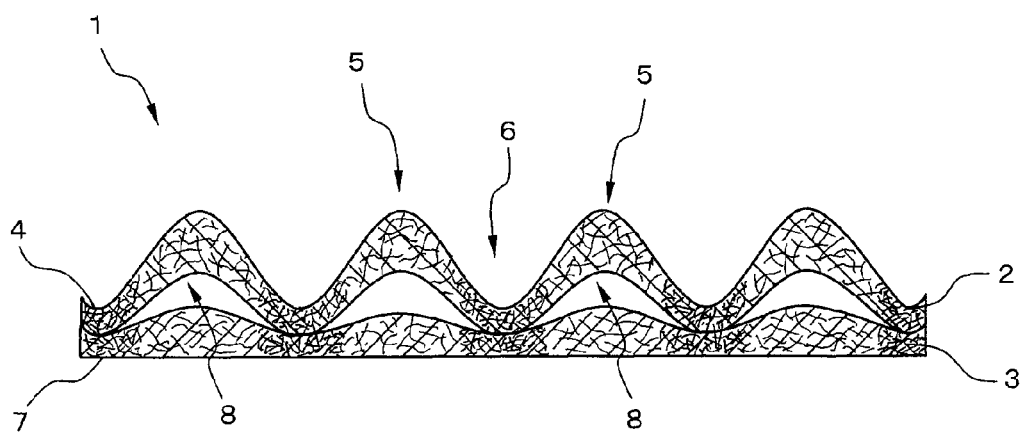
FIG. 4 is a cross-sectional view of another embodiment of the layered nonwoven fabric of the present disclosure.

According to another embodiment of the layered nonwoven fabric of the present disclosure, as shown in FIG. 3, the protrusions on the first surface may completely lack the aforementioned spades, or as shown in FIG. 4, the protrusions on the first surface may all have the spaces.

According to one embodiment of the layered nonwoven fabric of the present disclosure, the first nonwoven fabric has a maximum tensile strength that is equal to or less (weaker) than that of the second nonwoven fabric. A difference in the maximum tensile strengths will make it easier for the layered nonwoven fabric to have spaces, as explained in detail below in the production examples for the layered nonwoven fabric of the present disclosure.

The first nonwoven fabric and second nonwoven fabric may each be derived from an air-through nonwoven fabric, a spunbond nonwoven fabric, a point bond nonwoven fabric, a spunlace nonwoven fabric, an airlaid nonwoven fabric, a meltblown nonwoven fabric, or a nonwoven fabric comprising nanofibers. Examples of combinations of the first nonwoven fabric and second nonwoven fabric include a combination wherein the first nonwoven fabric is derived from an air-through nonwoven fabric and the second nonwoven fabric is derived from a spunbond nonwoven fabric, and a combination wherein the first nonwoven fabric is derived from an air-through nonwoven fabric and the second nonwoven fabric is derived from an air-through nonwoven fabric.

According to one embodiment of the layered nonwoven fabric of the present disclosure, the second surface may have a plurality of protrusions and a plurality of recesses, and according to another embodiment of the layered nonwoven fabric of the present disclosure, the layered nonwoven fabric may have one or more open holes connecting the recesses on the first surface and the recesses on the second surface. These open holes connecting the recesses may be formed when a surface of the nonwoven fabric is blasted with a sprayed fluid; for example when the second surface is blasted with fluid from spray nozzles.

The preferred range for the shapes of the open holes will differ depending on the purpose of use of the layered nonwoven fabric of the present disclosure. When the layered nonwoven fabric of the present disclosure is to be used in the top sheet of an absorbent article, the shapes of the open holes are preferably roughly circular in plan view, with diameters of about 0.1 to about 5.0 mm, and the open area is preferably about 1 to about 30%. This is from the viewpoint of permeability for body fluids and excreta upon absorption and back flow of absorbed body fluid and excreta.

The open area can be measured by photographing an image of a prescribed planar region of the layered nonwoven fabric that includes multiple open holes, the image being taken from a direction perpendicular to the planar direction, with enlargement of the image if necessary, calculating the area of open holes, and dividing this by the area of the prescribed region. The image is preferably taken of the surface of the nonwoven fabric which most clearly shows the open holes; for example, the surface of the nonwoven fabric which has been directly blasted by sprayed fluid.

The open holes have air-flow resistance of approximately 0 in the thickness direction, and have particularly excellent air permeability in the thickness direction of the layered nonwoven fabric. Also, since the open holes allow the structure to be altered during stretching, the strength is reduced during stretching and the fabric more easily follows movement of the body.

As used herein, "extendable fiber" means fiber having a low elastic limit, and more precisely a lower elastic limit than the stress that is applied during production of the layered nonwoven fabric, and that can undergo plastic deformation by stress during production. The extendable fiber becomes thinner and longer by plastic deformation. As used herein, extendable fiber that has undergone plastic deformation by the stress applied during production will also be referred to as "stretched extendable fiber". An example of a stretched extendable fiber is a fiber having a uniform diameter, or a fiber having a non-uniform diameter, such as one having partial thin sections (necking sections).

The first nonwoven fabric and the second nonwoven fabric are each composed of extendable fiber, meaning that the only type of fiber included in the first nonwoven fabric and second nonwoven fabric is extendable fiber. Thus, the first nonwoven fabric and second nonwoven fabric contain no elastic fiber, although they may contain an adhesive for anchoring between the fibers.

Examples of extendable fiber materials include fibers made of polyolefins, such as polyethylene and polypropylene, and polystyrenes, polyesters, polyamides, polyurethanes and polylactic acids, and combinations thereof. The extendable fiber may be a composite fiber, such as a core-sheath fiber or a side-by-side fiber.

The first nonwoven fabric and/or the second nonwoven fabric preferably consist of at least about 50% by mass, more preferably at least 70% by mass and even more preferably 100% by mass of the composite fiber. If the amount of composite fiber increases, the shapes of the recesses and protrusions on the first surface, i.e. the irregular shapes, will be resistant to collapse and air permeability along the recesses will tend to be satisfactory, for use as the top sheet of an absorbent article, even when body pressure is being applied by the wearer.

The extendable fiber may be fiber that is essentially hydrophilic, such as natural and/or semi-natural fiber. The extendable fiber is preferably fiber comprising polypropylene and polyethylene, from the viewpoint of low crystallinity and high ductility.

The fiber size of the extendable fiber is preferably in the range of about 1 to about 6 dtex, and more preferably in the range of about 5 to about 25 Dtex (or decitex) stands for the mass in grams of a fiber which is 10,000 m long.

When the layered nonwoven fabric is to be used in the liquid-permeable top sheet of an absorbent article, the layered nonwoven fabric, and more specifically the first nonwoven fabric and second nonwoven fabric, is preferably a nonwoven fabric with hydrophilicity. This will allow contacted hydrophilic excreta (urine, sweat, stool, etc.) to pass through the interior of the nonwoven fabric more easily without remaining on the surface of the nonwoven fabric.

Examples of nonwoven fabrics with hydrophilicity include nonwoven fabrics produced by treatment of the hydrophobic nonwoven fabric with a hydrophilic agent, nonwoven fabrics produced from composite fibers incorporating a hydrophilic agent, and nonwoven fabrics coated with a surfactant. Nonwoven fabrics with hydrophilicity also include nonwoven fabrics produced from fibers with innate hydrophilicity, such as natural and/or semi-synthetic fibers.

[Method for Producing Layered Nonwoven Fabric]

A method for producing the layered nonwoven fabric of the present disclosure will now be described.

Figure 5:
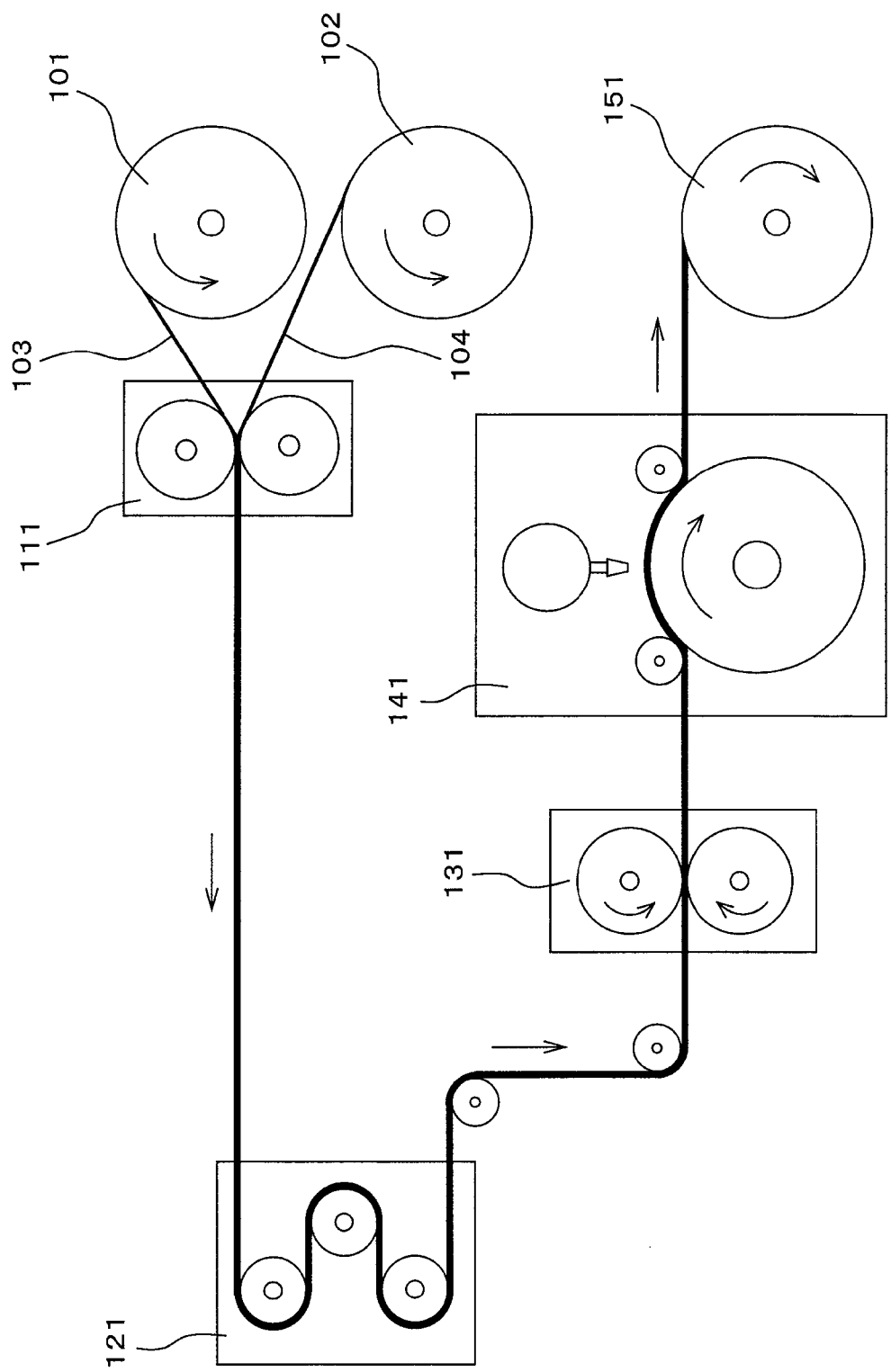
FIG. 5 is an illustration of an embodiment of a method for producing a layered nonwoven fabric.

FIG. 5 is an illustration of an embodiment of a method for producing a layered nonwoven fabric. FIG. 5 shows a first roll 101, a second roll 102, a laminating roll 111, a heating roll 121, a gear stretcher 131, a fluid treatment apparatus 141 and a take-up roll 151, which may be used to produce a layered nonwoven fabric. The method of the invention is not limited to these specific units or to their arrangement.

The method for producing the layered nonwoven fabric includes a step of preparing a first nonwoven fabric to be treated and a second nonwoven fabric to be treated.

As used herein, "first nonwoven fabric to be treated", "second nonwoven fabric to be treated" or "layered nonwoven fabric to be treated" is used to refer to the respective raw nonwoven fabric, i.e. the fabric before treatment, and forms the "first nonwoven fabric", "second nonwoven fabric" or "layered nonwoven fabric", respectively, after the non-homogeneous stretching step and fluid treatment step described hereunder.

The first nonwoven fabric to be treated and the second nonwoven fabric to be treated are not particularly restricted so long as they are made of extendable fiber, and for example, they may be a nonwoven fabric produced by any known method, such as an air-through nonwoven fabric, spunbond nonwoven fabric, point bond nonwoven fabric, spunlace nonwoven fabric, airlaid nonwoven fabric or melt-blown nonwoven fabric, or a nanofiber-containing nonwoven fabric. The combination of the first nonwoven fabric to be treated and second nonwoven fabric to be treated may be, for example, an air-through nonwoven fabric and spunbond nonwoven fabric or an air-through nonwoven fabric and air-through nonwoven fabric.

The first nonwoven fabric to be treated and second nonwoven fabric to be treated are each made of extendable fiber, and the extendable fiber may be selected from among the fibers mentioned below for the "layered nonwoven fabric", the fiber size of the extendable fiber is preferably selected in consideration of the fact that the fiber sizes become thinner during the subsequent steps.

Incidentally, the fact that the first nonwoven fabric to be treated and the second nonwoven fabric to be treated are each made of extendable fiber means that the only type of fiber included in the first nonwoven fabric to be treated and the second nonwoven fabric to be treated is extendable fiber. Thus, the first nonwoven fabric to be treated and the second nonwoven fabric to be treated contain no elastic fiber, although they may contain an adhesive for anchoring between the fibers.

The fiber lengths of the extendable fibers are not particularly restricted, and for example, the extendable fibers may be staple fibers or continuous filaments. When two or more fibers are included for the extendable fiber, the fiber lengths of the fibers may be the same or different.

The method for producing the layered nonwoven fabric of the present disclosure includes a step of layering the first nonwoven fabric to be treated on the second nonwoven fabric to be treated to form a layered nonwoven fabric to be treated.

This step may be carried out, as shown in FIG. 5 for example, by passing the first nonwoven fabric to be treated 103 which has been unwound from the first roll 101, over the second nonwoven fabric to be treated 104 which has been unwound from the second roll 102, through a laminating roll 111.

When nonwoven fabrics with different widths or nonwoven fabrics with different tensile strengths are to be layered, wrinkles tend to form in the produced layered nonwoven fabric, and therefore a hot-melt adhesive may be situated between the first nonwoven fabric to be treated and second nonwoven fabric to be treated, if desired, for temporary anchoring.

The method for producing a layered nonwoven fabric according to the present disclosure comprises a step in which the aforementioned layered nonwoven fabric to be treated is subjected to non-homogeneous stretching so as to form a layered nonwoven fabric having high-stretch regions and low-stretch regions (this will hereunder also be referred to as the "non-homogeneous stretching step").

The non-homogeneous stretching step is carried out on the layered nonwoven fabric to be treated, partially (i) to destroy the points of fiber contact of the extendable fibers of the first nonwoven fabric to be treated and second nonwoven fabric to be treated in the layered nonwoven fabric, and create a partial web state of the anchored fibers, and/or (ii) to form stretched extendable fibers between the points of fiber contact.

The stretched extendable fibers easily move when treated with a fluid, and therefore an irregular shape is easily formed in the layered nonwoven fabric that is to be formed.

Also, if gear stretching as described hereunder is employed in the non-homogeneous stretching step, (iii) the resistance of the fiber surfaces during stretching is increased at the sections of the continuous fibers with a large number of fibers where the extendable fibers are tangled, especially in the high-stretch regions, often resulting in local stretching of the fibers in the lengthwise direction and creation of neck sections.

The neck sections can serve as origins for fiber bending when pressure is applied, for example, and can therefore impart easy deformability to the layered nonwoven fabric, but because the neck sections are randomly distributed it is possible to maintain a certain degree of resistance to collapse.

The layered nonwoven fabric to be treated is preferably heated before the non-homogeneous stretching step with a heating roll or infrared heater, such as shown in FIG. 5. Heating of the layered nonwoven fabric to be treated renders the extendable fibers more susceptible to plastic deformation during the non-homogeneous stretching step, thereby preventing breakage and shedding of the extendable fibers.

Heating with the heating roll is preferably no higher than the melting point of the extendable fibers composing the layered nonwoven fabric to be treated, and may be near a temperature at which the endothermic peak begins to develop during DSC (Differential Scanning calorimetry) measurement.

The points of contact may be heat sealing points, in the case of an air-through nonwoven fabric, or they may be thermocompression bonding points in the case of a spunbond nonwoven fabric or point bond nonwoven fabric, or fiber tangling points in the case of a spunlace nonwoven fabric.

As used herein, "high-stretch region" means a region that has been stretched so that the degree of stretching of the stretched extendable fiber is higher than in the low-stretch regions, while "low-stretch region" means a region that has been stretched so that the degree of stretching of the stretched extendable fiber is lower than in the high-stretch regions, and it includes regions in which no stretched extendable fiber has been formed, i.e. unstretched regions.

Also as used herein, the term "non-homogeneous stretching" refers to stretching so as to form a layered nonwoven fabric having high-stretch regions and low-stretch regions, or in other words, stretching so as to form a layered nonwoven fabric having different degrees of stretching of the stretched extendable fiber, depending on the location.

The non-homogeneous stretching step may employ any desired means without any particular restrictions, so long as it allows formation of a layered nonwoven fabric having high-stretch regions and low-stretch regions, and it may be carried out using a gear stretcher, for example.

A gear stretcher is a pair of gear rolls with a rotational axis line perpendicular to the machine direction, which may include a member that rotates while meshing with the plurality of teeth arranged around the peripheral surface of each gear roll, and passing a layered nonwoven fabric to be treated through the gap in the gear rolls of the gear stretcher (this will hereunder also be referred to as "gear stretching") allows the aforementioned non-homogeneous stretching step to be carried out.

Figure 6:
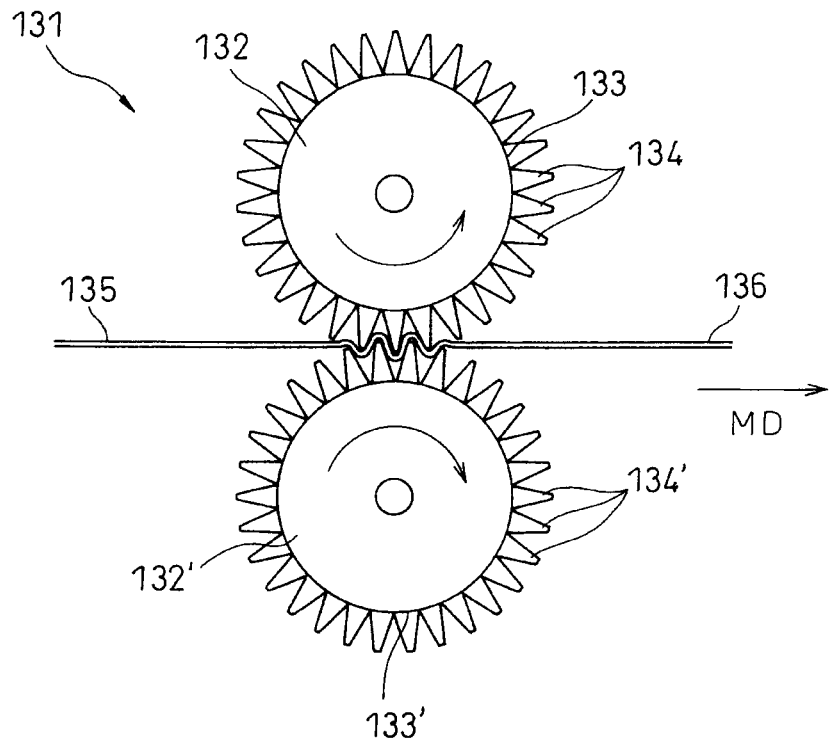
FIG. 6 is a schematic diagram showing an embodiment of a gear stretcher.

FIG. 6 is a schematic diagram showing an embodiment of a gear stretcher. The gear stretcher 131 shown in FIG. 6 has a pair of gear rolls 132 and 132'. A plurality of teeth 134 and 134' are arranged around the peripheral surfaces 133 and 133' of the gear rolls 132 and 132'. In the gear stretcher 131 shown in FIG. 6, the rotational axis lines of the gear rolls 132 and 132' are both perpendicular to the machine direction MD of the layered nonwoven fabric to be treated. The plurality of teeth 134 and 134' are arranged on the peripheral surfaces 133 and 133' in a manner parallel to the rotational axis lines.

In the gear stretcher 131 shown in FIG. 6, the layered nonwoven fabric to be treated 135 is passed through the roll gap between the pair of gear rolls 132 and 132', and when it passes through the gear rolls 132 and 132', the layered nonwoven fabric to be treated 135 is stretched by the mutually engaging plurality of teeth 134 and 134' of the gear rolls 132 and 132', on the three-point bending principle, to form a layered nonwoven fabric 136 having high-stretch regions and low-stretch regions. The layered nonwoven fabric 136 having high-stretch regions and low-stretch regions has alternating high-stretch regions and low-stretch regions in the machine direction MD, which are parallel to the direction that is perpendicular to the machine direction (hereunder, the direction perpendicular to the machine direction will also be referred to simply as the "cross-machine direction").

In the layered nonwoven fabric to be treated 135, the fabric of the layered nonwoven fabric is anchored in the regions that are in contact with the tips of the plurality of teeth 134 and 134', and therefore undergoes little or no stretching, forming the low-stretch regions. On the other hand, the regions of the layered nonwoven fabric to be treated 135 that do not contact the tips of the plurality of teeth 134 and 134', i.e. the regions between the tips of the teeth 134 and the tips of the teeth 134', are widely stretched to form high-stretch regions.

Figure 7:
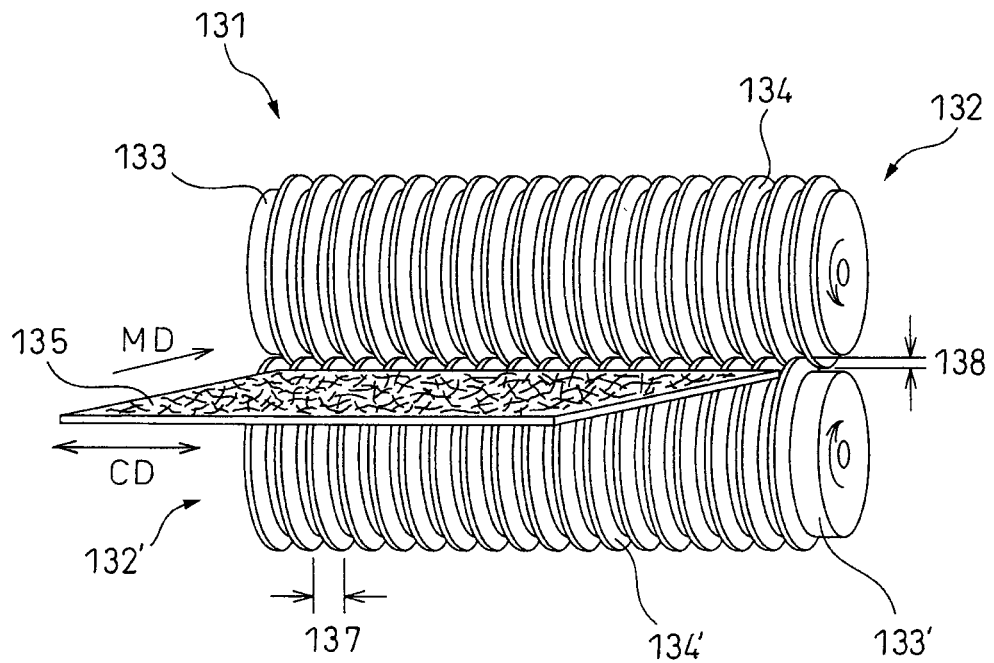
FIG. 7 is a schematic diagram showing another embodiment of a gear stretcher.

Gear stretching can also be accomplished using a gear stretcher as shown in FIG. 7.

FIG. 7 is a schematic diagram showing another embodiment of a gear stretcher. The gear stretcher 131 shown in FIG. 7 has a pair of gear rolls 132 and 132'. A plurality of teeth 134 and 134' are arranged around the peripheral surfaces 133 and 133' of the gear rolls 132 and 132'. In the gear stretcher 131 shown in FIG. 7, the plurality of teeth 134 and 134' are arranged on the respective peripheral surfaces 133 and 133' in a manner perpendicular to the rotational axis lines of the gear rolls 132 and 132'. When the plurality of teeth 134 and 134' are arranged perpendicular to the rotational axis lines in this manner, it is possible to form a layered nonwoven fabric having parallel high-stretch regions and low-stretch regions, each parallel to the machine direction MD, alternating in the cross-machine direction CD.

Figure 8:
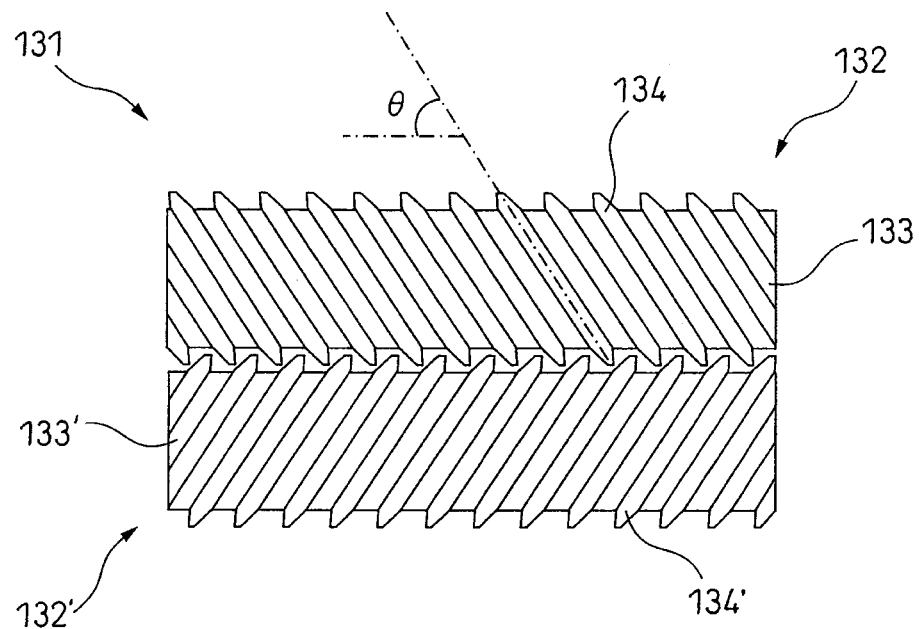
FIG. 8 is a schematic diagram showing another embodiment of a gear stretcher.

The gear stretching may also be accomplished using a gear stretcher having a plurality of teeth arranged around the peripheral surfaces of gear rolls, and slanted (inclined) with respect to the rotational axis lines of the gear rolls, as shown in FIG. 8. FIG. 8 is a schematic diagram showing another embodiment of a gear stretcher. The gear stretcher 131 shown in FIG. 8 has a pair of gear rolls 132 and 132', with a plurality of teeth 134, 134' arranged around the peripheral surfaces 133, 133' of the gear rolls 132, 132'. In the gear stretcher 131 shown in FIG. 8, the rotational axis lines of the gear rolls 132 and 132' are both perpendicular to the machine direction MD of the layered nonwoven fabric to be treated. The plurality of teeth 134 and 134' are arranged around the peripheral surfaces 133 and 133' at a fixed angle of $\theta$ with respect to the rotational axis line.

In the gear stretcher shown in FIG. 8, one tooth 134 and one tooth 134' may be situated on the peripheral surfaces 133 and 133' of the gear rolls 132 and 132', depending on the angle of $\theta$ and the gear pitch.

The gear stretcher may be appropriately selected depending on the desired performance for the layered nonwoven fabric to be formed.

The layered nonwoven fabric to be treated may be stretched several times using a gear stretcher, such as shown in FIG. 6 to FIG. 8.

In these gear stretchers, the gear pitch is preferably about 1-10 mm and more preferably about 2-6 mm. If the gear pitch is less than about 1 mm it may be necessary to reduce the thickness of the gear teeth and portions of the layered nonwoven fabric to be treated may become partially severed, while if the gear pitch is greater than about 10 mm, the draw ratio may be reduced and it may become difficult for the extendable fiber to be stretched.

The gear pitch is the interval between one tooth and another tooth, and it is denoted by numeral 137 in FIG. 7.

In this gear stretcher, the gear tooth cutting depth is preferably about 0.5 mm or greater. If the gear tooth cutting depth is less than about 0.5 mm, stretching of the layered nonwoven fabric may be inadequate and the extendable fiber may become difficult to stretch.

The gear tooth cutting depth is the depth at the section where the top gear roll tooth and bottom gear roll tooth overlap, and it is denoted by numeral 138 in FIG. 7.

In a layered nonwoven fabric having high-stretch regions and low-stretch regions, the draw ratio for each gear stretching is preferably about 30-400% and more preferably about 50-200%. If the draw ratio is lower than about 30% the extendable fiber may not be stretched, and if the draw ratio is higher than about 400%, the strength of the layered nonwoven fabric with high-stretch regions and low-stretch regions will tend to be weakened and the extended extendable fiber will tend to be shed preferentially, often causing transport problems, and/or the extendable fiber may undergo breakage.

As used herein, the term "draw ratio" refers to the value calculated by the following formula:

$$\text{Stretch ratio } (\%) = 100 \times \left[ \frac{\sqrt{P^2 + 4D^2}}{P} - 1 \right] \quad \text{[Formula 1]}$$

where P is the gear pitch and D is the gear tooth cutting depth.

Figure 9:
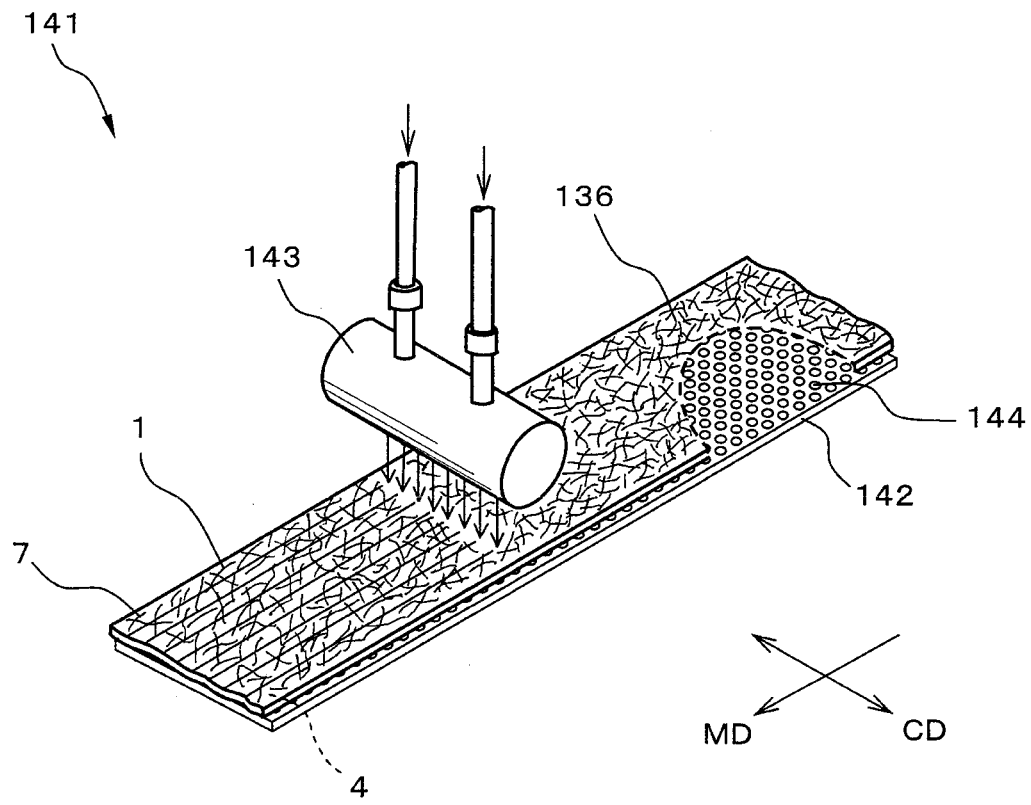
FIG. 9 is a diagram showing a fluid treatment apparatus to be used in an embodiment of the method for producing a layered nonwoven fabric according to the present disclosure.

The method for producing the layered nonwoven fabric comprises a step of placing the layered nonwoven fabric having high-stretch regions and low-stretch regions on a support, with the first surface contacting the support, and blasting a sprayed fluid onto the second surface for treatment to form a layered nonwoven fabric (this will hereunder be referred to as "fluid treatment step"). The fluid treatment step may be carried out using a fluid treatment apparatus 141 with a roll-like support, such as shown in FIG. 5, or using a fluid treatment apparatus 141 with a flat support, such as shown in FIG. 9.

With at least a portion of the webbed extendable fibers and/or stretched extendable fibers present in the high-stretch regions, which are formed in the non-homogeneous stretching step, at least some of the webbed extendable fibers and/or stretched extendable fibers on the side opposite the side on which fluid impacts (this will hereunder be referred to as the "non-fluid-impacting side", and it corresponds to the first surface of the layered nonwoven fabric) move along with the flow of fluid passing through the layered nonwoven fabric which has high-stretch regions and low-stretch regions, forming a plurality of protrusions and recesses on the non-fluid-impacting side, i.e. the first surface of the layered nonwoven fabric.

The support to be used to support the layered nonwoven fabric having high-stretch regions and low-stretch regions may be a support having openings and a fixed thickness, for example, openings of predetermined shape (for example, circular) arranged in a predetermined pattern in plan view (for example, a zigzag pattern), and for example, it may be a support having a plurality of roughly circular openings arranged in a zigzag pattern.

Specific examples of supports include metal, plastic or other punching plates, conveyor nets and paper making nets.

Specific examples of punching plates include those wherein open holes with predetermined shapes, for example, roughly circular, circular, roughly square, square, roughly rectangular or rectangular openings, are arranged in a predetermined pattern, such as 60° zigzag, square zigzag or a serial pattern, or another specific pattern, such as a heart-shaped pattern.

FIG. 9 is a diagram showing a fluid treatment apparatus to be used in an embodiment of the method for producing a layered nonwoven fabric according to the present disclosure, and the fluid treatment apparatus 141 shown in FIG. 9 has a support 142, a fluid nozzle 143 (comprising a plurality of sub-nozzles), and a fluid-receiving suction section (not shown) provided directly under the fluid nozzle 143. The support 142 is a punching plate having round hole openings 144 arranged in a zigzag pattern in plan view.

When the fluid treatment apparatus 141 shown in FIG. 9 is used for the fluid treatment step, it is possible to produce a layered nonwoven fabric having a plurality of protrusions arranged in a zigzag pattern on the first surface, as shown in FIG. 1.

The reason for this is as follows.

When fluid sprayed from the fluid nozzle reaches the support, it flows into the suction section through the openings. As a result, since the stretched extendable fibers, which have a high degree of freedom, collect in the openings of the support, the fibers become compacted and consequently the basis weight of the layered nonwoven fabric is increased, such that a plurality of protrusions are formed on the first surface. Because the stretched extendable fibers tend to rise in the thickness direction of the layered nonwoven fabric at the protrusions on the first surface, the layered nonwoven fabric is imparted with compression resistance, as well as improved fluid take-up and liquid permeability properties. In addition, the plurality of protrusions on the first surface results in excellent air permeability of the layered nonwoven fabric of the disclosure, particularly excellent air permeability in the planar direction, and superior feel on the skin due to reduced contact area.

When the support described above is used, recesses are formed in the regions of the first surface of the layered nonwoven fabric that are not in contact with the openings of the support.

The support to be used to support the layered nonwoven fabric having high-stretch regions and low-stretch regions may also be a support with projections and depressions, such as a support with projections and depressions of predetermined shape and arrangement. By using a support having projections and depressions, it is possible to further improve the air permeability, feel on the skin (for example, low contact area) and liquid uptake properties of the layered nonwoven fabric.

As used herein, a "projection" is a section used to form a plurality of furrows on the first surface of the layered nonwoven fabric, and a "depression" is a section used to form a plurality of ridges on the first surface of the layered nonwoven fabric.

Figure 10:
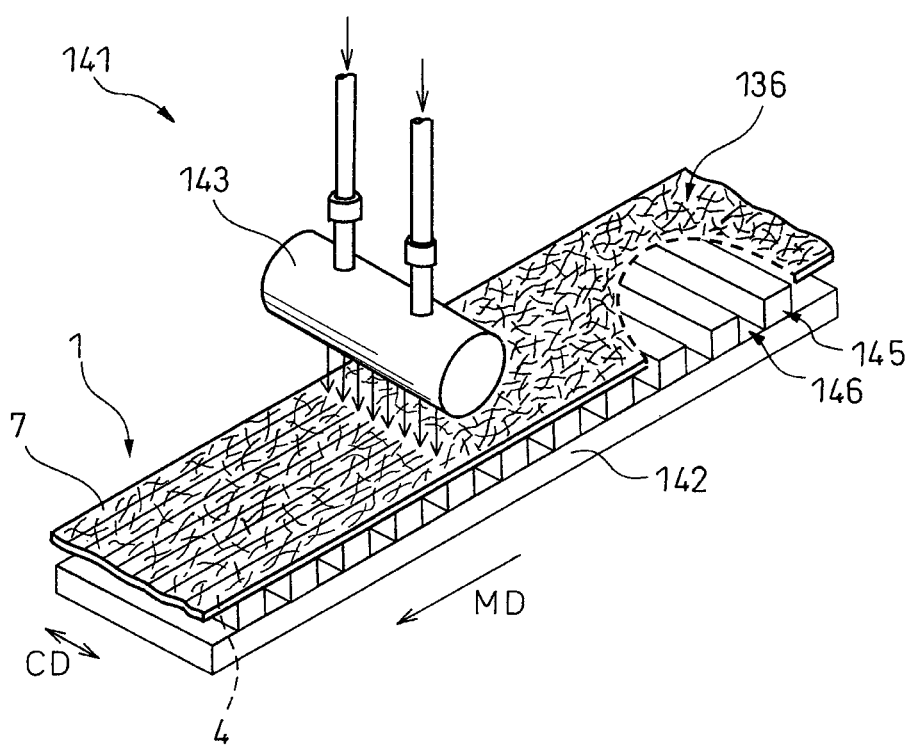
FIG. 10 is a diagram showing a fluid treatment apparatus to be used in an embodiment of the method for producing a layered nonwoven fabric according to the present disclosure.

FIG. 10 is a diagram showing a fluid treatment apparatus to be used in an embodiment of the method for producing a layered nonwoven fabric according to the present disclosure. The fluid treatment apparatus 141 shown in FIG. 10 is the same as the fluid treatment apparatus 141 shown in FIG. 9, except for having a different shape for the support 142.

In FIG. 10, the support 142 has a plurality of projections 145 and a plurality of depressions 146 running parallel to the cross-machine direction CD, and the projections 145 and depressions 146 are arranged in an alternating fashion in the machine direction MD. In this support 142, the projections 145 and depressions 146 have cubic shapes.

Also, while in FIG. 10 the projections 145 and depressions 146 are arranged parallel to the cross-machine direction CD and alternating in the machine direction MD, according to a different embodiment of the method for producing the layered nonwoven fabric, for example, the projections 145 and depressions 146: (i) may be projections and depressions that are all parallel to the machine direction and alternatingly disposed in the cross-machine direction, (ii) may be projections and depressions that are slanted (inclined) with respect to the machine direction and alternatingly disposed in the direction perpendicular to the slanted direction, or (iii) may be projections and/or depressions having predetermined shapes (for example, cubic, cylindrical or hemispherical) that are disposed in a predetermined arrangement (for example, a heart-shaped or star-shaped arrangement).

When a support having projections and depressions is used, it is possible to form a layered nonwoven fabric with a larger plurality of protrusions and deeper plurality of recesses (with one or more open holes depending on the case), than when using a support without projections and depressions.

Incidentally, for production of the surface sheet described in PTL 1, increasing the thickness has been associated with problems, such as reduced sheet strength and poor productivity, but in the method for producing a layered nonwoven fabric according to the present disclosure, the shape of the support, the fluid pressure and other factors may be adjusted to vary the thickness while maintaining strength. Furthermore, since the method for producing a layered nonwoven fabric according to the present disclosure includes a non-homogeneous stretching step and a fluid treatment step which allow simple and high-speed treatment to be carried out, it has excellent productivity.

The reason for this will now be explained in detail with reference to FIG. 10. When the fluid sprayed from the fluid nozzle 143 impacts the projections 145, it flows into and around the depressions 146. As a result, stretched extendable fibers with a high degree of freedom moves toward the depressions 146 with the flow of the fluid, and therefore compactness of the fibers is reduced at the sections where the fluid and projections 145 cross, resulting in reduction in the basis weight of the layered nonwoven fabric, and formation of a plurality of groove-shaped recesses (furrows) on the first surface 4. When the blasting force of the fluid is high, one or more open holes are sometimes formed connecting the recesses on the first surface 4 and the recesses on the second surface 7.

The recesses on the second surface will now be described.

Since the stretched extendable fibers collect at the locations where the fluid and depressions 146 cross, the fibers become compact and consequently the basis weight of the layered nonwoven fabric is increased, such that a plurality of ridge-shaped protrusions (ridges) are formed on the first surface 4. Since the stretched extendable fibers tend to rise in the thickness direction of the layered nonwoven fabric at the plurality of protrusions on the first surface 4, the layered nonwoven fabric is imparted with compression resistance, as well as improved fluid take-up and liquid permeability properties. In addition, since the layered nonwoven fabric 1 shown in FIG. 10 has a plurality of protrusions on the first surface 4, it has excellent air permeability, and especially air permeability in the planar direction, and has superior feel on the skin due to its low contact area.

A layered nonwoven fabric formed using a support having projections and depressions has, on the first surface, a plurality of ridged-shaped protrusions with heights that are higher and a plurality of groove-shaped recesses with depths that are deeper, compared to a layered nonwoven fabric formed using a support without projections and depressions, such as a support having openings and a fixed thickness, and it therefore exhibits excellent air permeability, and especially air permeability in the planar direction, as well as excellent compression resistance, fluid take-up properties and feel on the skin.

When the layered nonwoven fabric formed using a support having projections and depressions has one or a plurality of open holes, the air permeability in the thickness direction is excellent.

Of the air permeability in the planar directions, the layered nonwoven fabric formed using the support shown in FIG. 10 has particularly excellent air permeability in the cross-machine direction. This is because the groove-shaped recesses on the first surface of the layered nonwoven fabric can serve as gas channels.

The projections preferably have lower fluid permeability than the fluid permeability of the depressions. This is because with low fluid permeability at the projections, the fluid impacting the projections will flow toward the depressions, thus allowing formation of a plurality of protrusions of greater height on the second surface of the layered nonwoven fabric formed by the method described above.

The material of the projections may be metal, plastic or the like.

There are no particular restrictions on the support having projections and depressions with a predetermined shape and arrangement, and it may be formed by situating a member with a predetermined shape (such as cubic or tubular) in a predetermined arrangement, maintaining a fixed spacing, for example, on a metal or plastic conveyor net, paper-making net or punching plate that is commonly used as a fluid-permeable support.

Also, the support having projections and depressions with a predetermined shape and arrangement may be formed by situating cubic, cylindrical or hemispherical projections and/or depressions with predetermined shapes in a predetermined arrangement, such as in a heart-shaped or star-shaped pattern, on a metal or plastic conveyor net, paper-making net or punching plate, and for example, hemispherically-shaped metal may be situated on a punching plate with openings, in a predetermined arrangement (such as a heart-shaped pattern). When such a support is used, it is possible to form a layered nonwoven fabric having recesses in a predetermined pattern (for example, a heart-shaped pattern) on the first surface.

In a support having projections and depressions, their widths will differ depending on the properties required for the layered nonwoven fabric that is to be formed, but as an example, the support shown in FIG. 10 preferably has projection widths in the range of about 0.5 to about 10 mm, and depression widths in the range of about 1 to about 10 mm.

The fluid treatment step may also be carried out in a fluid treatment apparatus with a roll-like support, as shown in FIG. 5, and the support may be one having openings and a fixed thickness or a support with projections and depressions, similar to the support described above, instead of a roll-like support.

At least a portion of the webbed extendable fiber and/or stretched extendable fiber present in the high-stretch regions, formed in the non-homogeneous stretching step, is blasted with the sprayed fluid on the side that impacts with the fluid (hereunder referred to as "fluid-impacting side", and this corresponds to the second surface of the layered nonwoven fabric), and when the fluid impact energy is high, it is then rebounded and separated out in a planar direction, such as the cross-machine direction. More specifically, at the sections where the sprayed fluid has been blasted, the stretched extendable fiber moves into the areas where the fluid has not been blasted, often forming a plurality of protrusions and recesses on the fluid-impacting side, i.e. the second surface.

The fluid used in the fluid treatment step may be air, such as heated air or water vapor, such as saturated steam or superheated steam, or water, such as hot water.

The fluid may be blasted from an anchored fluid nozzle onto the layered nonwoven fabric having high-stretch regions and low-stretch regions, or it may be blasted from a fluid nozzle which has reciprocating motion in the cross-machine direction. The fluid may also be continuously or intermittently blasted from a fluid nozzle onto the layered nonwoven fabric having high-stretch regions and low-stretch regions. These may also be used in combination to form a plurality of protrusions and a plurality of recesses on the first surface of the layered nonwoven fabric (and the second surface if desired), having different patterns including a predetermined pattern.

The fluid may be appropriately selected depending on the state of the layered nonwoven fabric having high-stretch regions and low-stretch regions. For example, for treatment of a nonwoven fabric with a low gear pitch and a large draw ratio, air or water vapor is preferably selected as the fluid as this will allow movement of primarily the stretched extendable fiber with relatively low energy. Furthermore, since the joining points between fibers are increased in number when treating a nonwoven fabric with a large gear pitch and many low-stretch regions, a relatively high energy is necessary for movement of the stretched extendable fiber, and therefore water or water vapor is preferably selected as the fluid, with water vapor being more preferred. This is because moisture does not easily remain in the sections with a large composite fiber content and the joining points between the sections with a high composite fiber content are not usually destroyed, so that the stretched extendable fibers in the sections that are to undergo movement can easily move.

In the fluid treatment step, the distance between the tip of the fluid nozzle and the support is preferably in the range of about 1 to about 10 mm. If the distance is less than about 1 mm, the fibers will tend to adhere onto the nozzle, impairing productivity, while if the distance is greater than about 10 mm, the fluid energy may not sufficiently reach the extendable fibers and extension and movement of the extendable fibers will tend to be inadequate.

When the fluid is heated air, the pressure is preferably between about 0.01 and about 0.1 MPa and the temperature is preferably between about 100° C. and 300° C., when the fluid is saturated steam the pressure is preferably between about 0.1 and about 0.8 MPa and the temperature is preferably between about 100° C. and 170° C., and when the fluid is superheated steam the pressure is preferably between about 0.1 and about 0.8 MPa and the temperature is preferably between about 100° C. and 300° C.

Depending on the positional relationship between the fluid nozzle and the openings of the support, spaces 8 may be formed, such as shown in FIG. 2 and FIG. 4. For example, when the centers of the openings of the support are directly under the fluid nozzle, the nonwoven fabrics of the upper layer and lower layer will both be pushed into the openings of the support by the fluid, such that spaces will not easily be formed between the upper layer and lower layer. On the other hand, when the perimeters of the openings of the support are directly under the fluid nozzle, for example, the nonwoven fabric on the support side (upper layer) will tend to be pushed into the openings of the support, but the nonwoven fabric on the fluid nozzle side (lower layer) will not easily be pushed into the openings of the support, thus tending to produce spaces between the upper layer and lower layer.

The layered nonwoven fabric of the present disclosure is useful as an absorbent article, such as a sanitary product, disposable diaper, incontinence pad, panty liner or the like, a cleaning product, such as a wiper or wipe, or a medical product, such as a mask. The layered nonwoven fabric of the present disclosure is especially useful as the top sheet of an absorbent article.

EXAMPLES

The disclosure will now be explained in greater detail using examples and comparative examples, with the understanding that the disclosure is in no way limited by the examples.

The evaluated properties and measuring conditions in the examples and comparative examples were as follows.

[Basis Weight]

The masses of 10 samples of 100 mm×300 mm size were measured, and then the mass (g) of each sample was divided by the area ($m^2$) of the sample to calculate the basis weight of each sample. The mean value for the basis weights of the 10 samples was then calculated, and the mean value was used as the basis weight.

[Bulk]

The bulk was measured using a THICKNESS GAUGE UF-60 by Daiei Kagaku Seiki Mfg. Co., Ltd. With the UF-60, pressure of 3 $gf/cm^2$ is applied to the sample and the thickness is measured, to calculate the bulk.

[Expansion Property]

This was measured using a Model AG-1KNI autograph tensile tester by Shimadzu Corp., in the following manner.

—5% Tensile Strength—

A 50 mm sample was anchored to a chuck with a chuck distance of 100 mm, and the sample was then extended at a rate of 100 mm/min until it tore. The strength per 50 mm width during 5% extension was recorded as the 5% tensile strength.

In Table 1, the MD 5% tensile strength is the value of the tensile strength measured in the machine direction during production of air-through nonwoven fabrics No. 1 and No. 2 in cases without treatment. In cases with treatment (gear stretching+water vapor, or heat embossing), it is the tensile strength measured in the machine direction after treatment, matching the machine direction during production of the air-through nonwoven fabric with the machine direction during treatment.

The CD 5% tensile strength is the value of the tensile strength measured in the cross-machine direction during production of air-through nonwoven fabrics No. 1 and No. 2 in cases without treatment. In cases with treatment (gear stretching+water vapor, or heat embossing), it is the tensile strength measured in the cross-machine direction after treatment, matching the cross-machine direction during production of the air-through nonwoven fabric with the cross-machine direction during treatment.

Here, "N/50 mm", for the tensile strength in Table 1, means the tensile strength (N) per 50 mm width.

—Maximum Tensile Strength—

A 50 mm sample was anchored to a chuck with a chuck distance of 100 mm, and the sample was then extended at a rate of 100 mm/min until it tore. The maximum strength in the measurement was evaluated as the maximum tensile strength.

In Table 1, MD and CD, for the MD maximum tensile strength and CD maximum tensile strength, have the same meanings as for the 5% tensile strength.

—Compression Property—

The compression property was measured using a KES-FB3 automated compression tester by Kato Tech Corp.

The measuring conditions were as follows.
SENS: 2
Speed: 0.02 mm/sec
Stroke: 5 mm/10 V
Compression area: 2 cm$^2$
Uptake interval: 0.1 second
Load limit: 50 g/cm$^2$
Repeat frequency: 1

The compression property may be evaluated from WC representing the compressional energy per 1 cm$^2$ of nonwoven fabric, RC representing the recoverability, $T_0$ representing the thickness of the sample at a pressure of 0.5 gf/cm$^2$, and $T_m$ representing the thickness of the sample at a pressure of 50 gf/cm$^2$. A larger WC value indicates greater ease of compression, while an RC value closer to 100% indicates higher recoverability.

[Liquid Permeability]

The liquid permeability was evaluated using a LISTER strike-through tester by Lenzing AG. The evaluation procedure was as follows.

(1) The sample, cut to a size of 100×100 mm, was placed on 5 sheets of filter paper (Advantec Filter Paper Grade 2) cut to sizes of 100×100 mm, and an electrical liquid permeation plate was placed thereover.

(2) The filter paper, sample and electrical liquid permeation plate were set on the strikethrough tester.

(3) A 5 mL portion of physiological saline was poured into the strikethrough tester.

(4) The physiological saline (room temperature) was allowed to drop from the strikethrough tester through an open hole in the electrical liquid permeation plate.

(5) The electrification time of the electrical liquid permeation plate was recorded.

(6) The measurement was repeated three times and the average value of these was recorded as the liquid permeation time.

When no sample was set, i.e. with only 5 filter paper sheets, the liquid permeation time was 69 seconds.

Production Example 1

Production of Layered Nonwoven Fabric

As the first nonwoven fabric there was prepared an air-through nonwoven fabric No. 1 (basis weight: 23 g/m$^2$, fibers: polyethylene/polyester composite fibers, fiber size: 2.2 dtex), and as the second nonwoven fabric there was prepared an air-through nonwoven fabric No. 2 (basis weight: 20 g/m$^2$, fibers: polyethylene/polyester composite fibers, fiber size: 2.2 dtex), and the layered nonwoven fabric to be treated No. 1 was formed by stacking the first non woven fabric over the second nonwoven fabric.

—Gear Stretching Treatment—

The layered nonwoven fabric to be treated No. 1 was reeled out at a speed of 50 m/min and subjected to gear stretching using a gear stretcher, such as shown in FIG. 7 (gear pitch: 1.5 mm, gear tooth cutting depth: 1.4 mm, gear tip width: 0.2 mm, gear temperature: 60° C.), to a draw ratio of 111.8% in the cross-machine direction CD, to form layered nonwoven fabric No. 1 having high-stretch regions and low-stretch regions.

—Steam Treatment—

Layered nonwoven fabric No. 1 having high-stretch regions and low-stretch regions was subjected to steam treatment using the fluid treatment apparatus shown in FIG. 9. Specifically, layered nonwoven fabric No. 1 having high-stretch regions and low-stretch regions was placed on a support made of a round-hole 60°-zigzag punching plate (diameter ϕ: 3.0 mm, MD pitch: 6.93 mm, CD pitch: 4.0 mm, thickness: 0.5 mm), and passed under a fluid nozzle comprising a plurality of nozzles (diameter ϕ: 0.5 mm) at 1.0 mm spacings (spray pressure: 0.50 Mpa, water vapor temperature: approximately 149° C.) at a speed of 50 m/min while maintaining a distance of 5.0 mm between the nozzle and the support, to obtain nonwoven fabric No. 1.

The properties of nonwoven fabric No. 1 are shown in Table 1. A cross-section of nonwoven fabric No. 1 is shown in FIG. 11.

Figure 11:
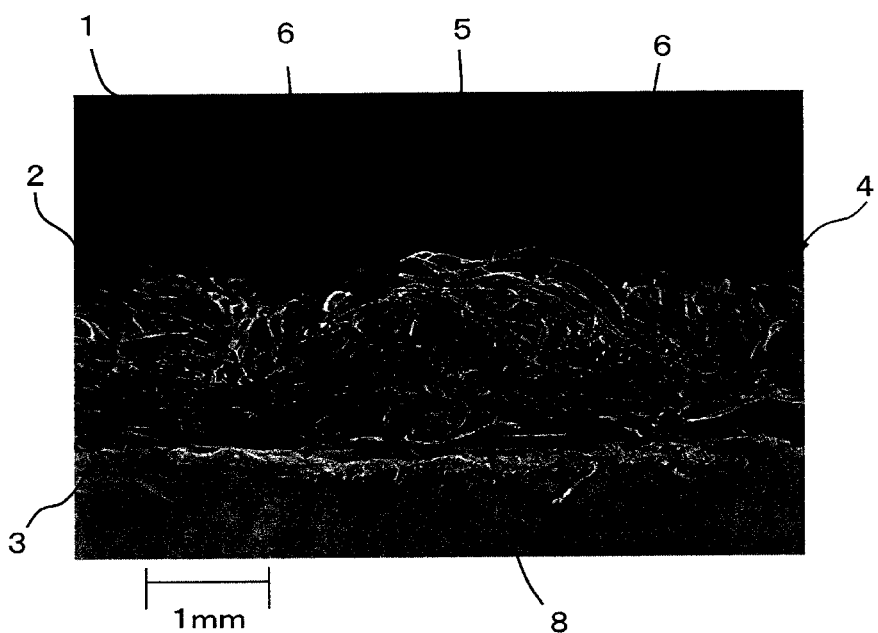
FIG. 11 is an electron micrograph of a cross-section of nonwoven fabric No. 1.

FIG. 11 suggests that, since the extended extendable fibers are oriented in the thickness direction at the protrusions 5 on the first surface 4, the contact area with the skin is reduced when the first surface is used as the skin contact surface on the top sheet of an absorbent article, thus allowing a smooth feel to be obtained. Also, since the extended extendable fibers are oriented in the thickness direction in the protrusions 5, the resistance to liquid permeability is low, suggesting high liquid permeability. Also, the interface between the first nonwoven fabric and second nonwoven fabric is indistinct in FIG. 11, suggesting that the extendable fibers of the first nonwoven fabric and the extendable fibers of the second nonwoven fabric were entangled.

Upon taking several cross-sectional photographs in addition to FIG. 11, it was possible to confirm that the protrusions on the first surface had lower fiber density than the recesses on the first surface in nonwoven fabric No. 1. Also, when the basis weight of the protrusions on the first surface and the recesses on the first surface were measured for nonwoven fabric No. 1, the protrusions on the first surface were confirmed to have a higher basis weight than the recesses on the first surface.

Also, the peel strength of nonwoven fabric No. 1 was 0.15 N/25 mm. Thus, the peel strength also suggested that the first nonwoven fabric and second nonwoven fabric of nonwoven fabric No. 1 were entangled.

Production Example 2

Nonwoven fabric No. 2 was produced according to the method described in Japanese Unexamined Patent Publication No. 2004-174234.

The properties of nonwoven fabric No. 2 are shown in Table 1. A cross-section of nonwoven fabric No. 2 is shown in FIG. 12.

Figure 12:
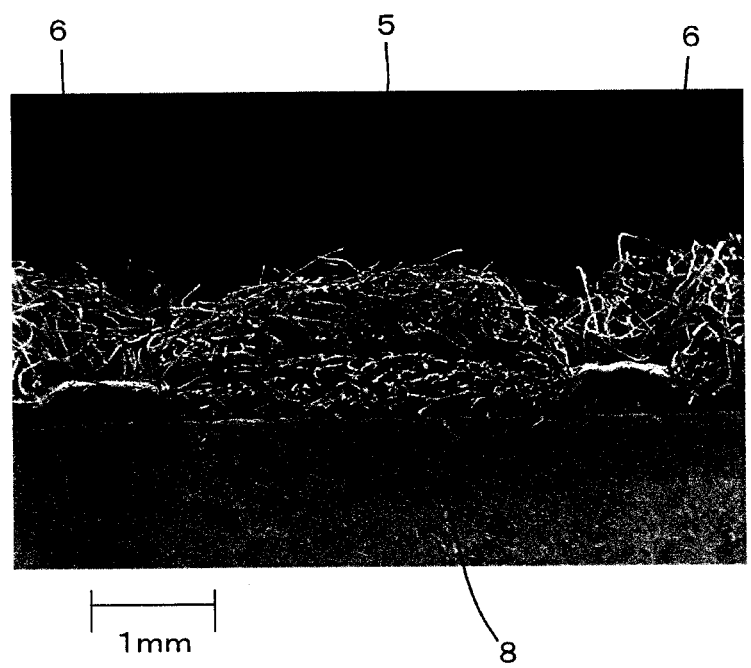
FIG. 12 is an electron micrograph of a cross-section of nonwoven fabric No. 2.

FIG. 12 shows that at the recesses 6 of nonwoven fabric No. 2, the two nonwoven fabrics were thermocompression bonded into a film by heat embossing, thus being integrated. Also, the top sections of the protrusions 5 in nonwoven fabric No. 2 are seen to be relatively flat. This is believed to reflect the shape of the gear used to form the irregularities. Thus, when nonwoven fabric No. 2 is used as the top sheet of an absorbent article, the contact area with the skin will not easily be reduced and a smooth feel will not easily be obtained. Moreover, since a small amount of fibers are supporting the protrusions in nonwoven fabric No. 2, the protrusions will presumably collapse easily when body pressure has been applied, thus tending to lower the liquid permeability.

Production Examples 3 and 4

Air-through nonwoven fabric No. 1 and air-through nonwoven fabric No. 2 were used as nonwoven fabric No. 3 and No. 4, respectively.

The properties of nonwoven fabrics No. 3 and No. 4 are shown in Table 1.

Production Examples 5 and 6

Air-through nonwoven fabric No. 1 and air-through nonwoven fabric No. 2 were subjected to gear stretching treatment and steam treatment as described in Production Example 1, to obtain nonwoven fabrics No. 5 and No. 6.

The properties of nonwoven fabrics No. 5 and No. 6 are shown in Table 1.

TABLE 1

| | | Nonwoven fabric No. | | | | | |
|---|---|---|---|---|---|---|---|
| | | 1 | 2 | 3 | 4 | 5 | 6 |
| Air-through nonwoven fabric No. 1 | | G | G | G | — | G | — |
| Air-through nonwoven fabric No. 2 | | G | G | — | G | — | G |
| Treatment | | Gear stretching + steam | Heat embossing | — | — | Gear stretching + steam | Gear stretching + steam |
| Basis weight | g/m$^2$ | 34.3 | 39.0 | 23.2 | 20.8 | 19.0 | 18.5 |
| Bulk | mm | 1.09 | 0.91 | 0.47 | 0.33 | 0.83 | 0.78 |
| MD 5% Tensile strength | N/50 mm | 6.6 | 4.8 | 5.8 | 8.0 | 2.7 | 3.0 |
| MD Maximum tensile strength | N/50 mm | 38.7 | 28.7 | 31.6 | 33.8 | 21.9 | 25.6 |
| CD 5% Tensile strength | N/50 mm | 0.6 | 0.4 | 0.2 | 0.2 | 0.0 | 0.0 |
| CD Maximum tensile strength | N/50 mm | 8.0 | 9.2 | 5.6 | 6.2 | 4.3 | 4.6 |
| Compression properties | WC (N∗m/m$^2$) | 1.2 | 0.9 | 0.4 | 0.3 | 1.1 | 1.0 |
| | RC (%) | 45 | 53 | 60 | 62 | 45 | 43 |
| | T$_o$ (mm) | 1.4 | 1.2 | 0.8 | 0.5 | 1.5 | 1.2 |
| | T$_m$ (mm) | 0.4 | 0.4 | 0.2 | 0.2 | 0.2 | 0.3 |
| Liquid permeability | sec | 1.7 | 6.6 | 13.1 | 19.7 | 2.6 | 3.2 |

Nonwoven fabric No. 1 was shown to have higher liquid permeability than nonwoven fabric No. 2 which was produced according to the method described in Japanese Unexamined Patent Publication No. 2004-174234. Also, nonwoven fabric No. 1 had higher bulk and a higher WC value than nonwoven fabric No. 2, and a reduced feeling of stiffness when contacted with the skin. In addition, since nonwoven fabric No. 1 had the same T$_m$ value as nonwoven fabric No. 2, the distance from the absorbent body is maintained even when body pressure is applied, thus reducing back flow of liquid from the absorbent body.

Furthermore, since the MD 5% tensile strength of nonwoven fabric No. 1 is higher than that of nonwoven fabric No. 2, it has less deformation when subjected to a constant tension, and has excellent transporting properties.

The present disclosure relates to the following J1 to J15.

[J1]
A layered nonwoven fabric comprising an upper layer consisting of a first nonwoven fabric and a lower layer consisting of a second nonwoven fabric,
wherein the first nonwoven fabric and second nonwoven fabric are each composed of extendable fibers, and some of the extendable fibers of the first nonwoven fabric are tangled with some of the extendable fibers of the second nonwoven fabric,
the layered nonwoven fabric has a first surface on the first nonwoven fabric side with a plurality of protrusions and recesses and a second surface on the second nonwoven fabric side,
the protrusions on the first surface have a higher basis weight than the recesses on the first surface, and
the protrusions on the first surface have a lower fiber density than the recesses on the first surface.

[J2]
The layered nonwoven fabric according to J1, wherein the first nonwoven fabric has a maximum tensile strength that is equal to or weaker than the second nonwoven fabric.

[J3]
The layered nonwoven fabric according to J1 or J2, wherein at least some of the protrusions on the first surface have spaces formed between the upper layer and lower layer.

[J4]
The layered nonwoven fabric according to any one of J1 to J3, wherein the first nonwoven fabric is derived from an air-through nonwoven fabric, and the second nonwoven fabric is derived from a spunbond nonwoven fabric.

[J5]
The layered nonwoven fabric according to any one of J1 to J4, wherein the extendable fibers of the first nonwoven fabric and/or second nonwoven fabric have a plurality of neck sections with partially narrowed diameters.

[J6]
The layered nonwoven fabric according to any one of J1 to J5, wherein the protrusions on the first surface are arranged in a zigzag pattern on the first surface.

[J7]
A layered nonwoven fabric according to any one of J1 to J6, wherein the second surface has a plurality of protrusions and a plurality of recesses, and the layered nonwoven fabric has one or more open holes connecting the recesses on the first surface and the recesses on the second surface.

[J8]
A layered nonwoven fabric formed by preparing a first nonwoven fabric to be treated and a second nonwoven fabric to be treated, forming a layered nonwoven fabric to be treated by stacking the first nonwoven fabric to be treated on the second nonwoven fabric to be treated, subjecting the layered nonwoven fabric to be treated to non-homogeneous stretching so as to form a layered nonwoven fabric having high-stretch regions and low-stretch regions, placing the layered nonwoven fabric having high-stretch regions and low-stretch regions on a support, with the first surface contacting the support, and blasting a sprayed fluid onto the second surface for treatment.

[J9]

A method for producing a layered nonwoven fabric according to any one of J1 to J8, the method comprising the steps of:

providing a first nonwoven fabric to be treated and a second nonwoven fabric to be treated, stacking the first nonwoven fabric to be treated on the second nonwoven fabric to be treated to form a layered nonwoven fabric to be treated, subjecting the layered nonwoven fabric to be treated to non-homogeneous stretching so as to form a layered nonwoven fabric having high-stretch regions and low-stretch regions, and forming a layered nonwoven fabric by placing the layered nonwoven fabric having high-stretch regions and low-stretch regions on a support, with the first surface contacting the support, and blasting a sprayed fluid onto the second surface for treatment.

[J10]

The method according to J9, wherein the step of non-homogeneous stretching is carried out by passing the layered nonwoven fabric to be treated through the gap between a pair of gear rolls with rotational axis lines that are perpendicular to the machine direction, and rotating while a plurality of teeth situated on the peripheral surfaces of each of the gear rolls are mutually engaged.

[J11]

The method according to J10, wherein the plurality of teeth are arranged on the peripheral surfaces in a manner perpendicular to the rotational axis lines so as to form the layered nonwoven fabric having high-stretch regions and low-stretch regions as a layered nonwoven fabric wherein the high-stretch regions and low-stretch regions each parallel to the machine direction are alternating in the cross-machine direction that is perpendicular to the machine direction, or the plurality of teeth are arranged on the peripheral surfaces in a manner parallel to the rotational axis lines so as to form the layered nonwoven fabric having high-stretch regions and low-stretch regions as a layered nonwoven fabric wherein the high-stretch regions and low-stretch regions each parallel to the direction perpendicular to the machine direction are alternating in the machine direction.

[J12]

The method according to any one of J9 to J11, wherein the support has a plurality of roughly circular openings arranged in a zigzag pattern.

[J13]

The method according to any one of J9 to J12, wherein the support has projections and depressions with predetermined shapes and arrangement on the side in contact with the first surface.

[J14]

The method according to any one of J9 to J13, wherein the first nonwoven fabric to be treated and the second nonwoven fabric to be treated are, respectively, an air-through nonwoven fabric and a spunbond nonwoven fabric.

[J15]

The method according to any one of J9 to J14, wherein the fluid is selected from the group consisting of air, water vapor and water.

In addition, the present disclosure relates to the following E1 to E15.

[E1]

A layered nonwoven fabric comprising an upper layer consisting of a first nonwoven fabric and a lower layer consisting of a second nonwoven fabric, wherein the first nonwoven fabric and second nonwoven fabric are each composed of extendable fibers, and some of the extendable fibers of the first nonwoven fabric are tangled with some of the extendable fibers of the second nonwoven fabric, the layered nonwoven fabric has a first surface on the first nonwoven fabric side with a plurality of protrusions and recesses and a second surface on the second nonwoven fabric side, the protrusions on the first surface have a higher basis weight than the recesses on the first surface, and the protrusions on the first surface have a lower fiber density than the recesses on the first surface.

[E2]

The layered nonwoven fabric according to E1, wherein the first nonwoven fabric has a maximum tensile strength that is equal to or less than the second nonwoven fabric.

[E3]

The layered nonwoven fabric according to E1 or E2, wherein at least some of the protrusions on the first surface have spaces formed between the upper layer and lower layer.

[E4]

The layered nonwoven fabric according to any one of E1 to E3, wherein the first nonwoven fabric is derived from an air-through nonwoven fabric, and the second nonwoven fabric is derived from a spunbond nonwoven fabric or from an air-through nonwoven fabric.

[E5]

The layered nonwoven fabric according to any one of J1 to J4, wherein the extendable fibers of the first nonwoven fabric and/or second nonwoven fabric have a plurality of neck sections with partially narrowed diameters.

[E6]

The layered nonwoven fabric according to any one of E1 to E5, wherein the protrusions on the first surface are arranged in a zigzag pattern on the first surface, in plan view

[E7]

A layered nonwoven fabric according to any one of E1 to E6, wherein the second surface has a plurality of protrusions and a plurality of recesses, and the layered nonwoven fabric has one or more open holes connecting the recesses on the first surface and the recesses on the second surface.

[E8]

A layered nonwoven fabric formed by preparing a first nonwoven fabric to be treated and a second nonwoven fabric to be treated, forming a layered nonwoven fabric to be treated by stacking the first nonwoven fabric to be treated on the second nonwoven fabric to be treated, subjecting the layered nonwoven fabric to be treated to non-homogeneous stretching so as to form a layered nonwoven fabric having high-stretch regions and low-stretch regions, placing the layered nonwoven fabric having high-stretch regions and low-stretch regions on a support, with the first surface contacting the support, and blasting a sprayed fluid onto the second surface for treatment.

[E9]

A method for producing a layered nonwoven fabric according to any one of E1 to E8, the method comprising the steps of:

providing a first nonwoven fabric to be treated and a second nonwoven fabric to be treated, stacking the first nonwoven fabric to be treated on the second nonwoven fabric to be treated to form a layered nonwoven fabric to be treated, subjecting the layered nonwoven fabric to be treated to non-homogeneous stretching so as to form a layered nonwoven fabric having high-stretch regions and low-stretch regions, and forming a layered nonwoven fabric by placing the layered nonwoven fabric having high-stretch regions and low-stretch regions on a support, with the first surface contacting the support, and blasting a sprayed fluid onto the second surface for treatment.

[E10]

The method according to E9, wherein the step of non-homogeneous stretching is carried out by passing the layered nonwoven fabric to be treated through the gap between a pair of gear rolls with rotational axis lines that are substantially perpendicular to the machine direction, and rotating the gear rolls while a plurality of teeth situated on the peripheral surfaces of each of the gear rolls are mutually engaged.

[E11]

The method according to E10, wherein the plurality of teeth are arranged on the peripheral surfaces in a manner substantially perpendicular to the rotational axis lines so as to form the layered nonwoven fabric having high-stretch regions and low-stretch regions as a layered nonwoven fabric wherein the high-stretch regions and low-stretch regions each parallel to the machine direction are alternating in the cross-machine direction that is perpendicular to the machine direction, or the plurality of teeth are arranged on the peripheral surfaces in a manner substantially parallel to the rotational axis lines so as to form the layered nonwoven fabric having high-stretch regions and low-stretch regions as a layered nonwoven fabric wherein the high-stretch regions and low-stretch regions each parallel to the direction perpendicular to the machine direction are alternating in the machine direction.

[E12]

The method according to any one of E9 to E11, wherein the support has a plurality of roughly circular openings arranged in a zigzag pattern in plan view.

[E13]

The method according to any one of E9 to E12, wherein the support has projections and depressions with predetermined shapes and a predetermined arrangement on the side in contact with the first surface.

[E14]

The method according to any one of E9 to E13, wherein the first nonwoven fabric to be treated and the second nonwoven fabric to be treated are, respectively, an air-through nonwoven fabric and a spunbond nonwoven fabric or are, respectively, an air-through nonwoven fabric and an air-through nonwoven fabric.

[E15]

The method according to any one of E9 to E14, wherein the fluid is selected from the group consisting of air, water vapor and water.

REFERENCES SIGNS LIST

1 Layered nonwoven fabric
2 Upper layer
3 Lower layer
4 First surface
5 Protrusion
6 Recess
7 Second surface
8 Space
101 First roll
102 Second roll
103 First nonwoven fabric to be treated
104 Second nonwoven fabric to be treated
111 Laminating roll
121 Heating roll
131 Gear stretcher
132,132' Gear rolls
133,133' Peripheral surfaces
134,134' Teeth
135 Layered nonwoven fabric to be treated
136 Layered nonwoven fabric having high-stretch regions and low-stretch regions
137 Gear pitch
138 Gear tooth cutting depth
141 Fluid treatment apparatus
142 Support
143 Fluid nozzle
144 Opening
145 Projection
146 Depression
151 Take-up roll
MD Machine direction
CD Cross-machine direction

The invention claimed is:

1. A layered nonwoven fabric comprising an upper layer consisting of a first nonwoven fabric and a lower layer consisting of a second nonwoven fabric,
   wherein the first nonwoven fabric and second nonwoven fabric are each composed of extendable fibers, and some of the extendable fibers of the first nonwoven fabric are tangled with some of the extendable fibers of the second nonwoven fabric,
   the layered nonwoven fabric has a first surface on the first nonwoven fabric side with a plurality of protrusions and recesses and a second surface on the second nonwoven fabric side,
   at least some of the protrusions on the first surface have spaces formed between the upper layer and lower layer,
   the protrusions on the first surface have a higher basis weight than the recesses on the first surface, and the protrusions on the first surface have a lower fiber density than the recesses on the first surface.

2. The layered nonwoven fabric according to claim 1, wherein the first nonwoven fabric has a maximum tensile strength that is equal to or weaker than the second nonwoven fabric.

3. The layered nonwoven fabric according to claim 1, wherein the first nonwoven fabric is derived from an air-through nonwoven fabric, and the second nonwoven fabric is derived from a spunbond nonwoven fabric.

4. The layered nonwoven fabric according to claim 1, wherein the extendable fibers of the first nonwoven fabric and/or second nonwoven fabric have a plurality of neck sections with partially narrowed diameters.

5. The layered nonwoven fabric according to claim 1, wherein the protrusions on the first surface are arranged in a zigzag pattern on the first surface.

6. A layered nonwoven fabric according to claim 1, wherein the second surface has a plurality of protrusions and a plurality of recesses, and the layered nonwoven fabric has one or more open holes connecting the recess on the first surface and the recess on the second surface.

7. The layered nonwoven fabric according to claim 2, wherein the first nonwoven fabric is derived from an air-through nonwoven fabric, and the second nonwoven fabric is derived from a spunbond nonwoven fabric.

8. The layered nonwoven fabric according to claim 2, wherein the extendable fibers of the first nonwoven fabric and/or second nonwoven fabric have a plurality of neck sections with partially narrowed diameters.

* * * * *